United States Patent [19]

Mateles et al.

[11] 3,989,595

[45] Nov. 2, 1976

[54] PRODUCTION OF SINGLE CELL PROTEIN

[76] Inventors: Richard Isaac Mateles, Jabotinsky 28; Israel Goldberg, Burla 26, both of Jerusalem; Emil Battat, Halperin 3, Herzliya, all of Israel

[22] Filed: Aug. 29, 1975

[21] Appl. No.: 609,164

[30] Foreign Application Priority Data

Sept. 3, 1974 Israel...................................... 45587

[52] U.S. Cl..................................... 195/49; 195/96
[51] Int. Cl.²......................................... C12D 13/06
[58] Field of Search............................... 195/49, 96

[56] References Cited

UNITED STATES PATENTS

| | | | |
|---|---|---|---|
| 3,546,071 | 12/1970 | Dours, Jr. et al..................... | 195/49 |
| 3,644,175 | 2/1972 | Dasinger et al. ......................... | 195/49 |
| 3,755,082 | 8/1973 | Terui et al. ............................ | 195/49 |
| 3,901,762 | 8/1975 | Yoshikawa et al. .................. | 195/49 |

OTHER PUBLICATIONS

Chalfan et al., Applied Microbiology, vol. 23, pp. 135–140 (1972).

*Primary Examiner*—Alvin E. Tanenholtz
*Attorney, Agent, or Firm*—Browdy and Neimark

[57] ABSTRACT

A process for the production of single cell protein which comprises growing on a suitable medium bacteria by continuous culture, said bacteria being capable of utilizing methanol, or methanol and formaldehyde, or methanol and formate as single carbon source. Preferred bacteria are *Pseudomonas C*, and a preferred culture medium contains 2.5 to 200 micrograms copper ions, calculated on metallic copper.

5 Claims, No Drawings

PRODUCTION OF SINGLE CELL PROTEIN

SUMMARY OF THE INVENTION

The present invention relates to a novel process for the production of single-cell protein. More particularly, the invention relates to the production of single-cell protein which can be used as protein supplement for animal feed purposes, for the isolation of cellular enzymes, growth factors and other cellular components and for other purposes where proteins of this type can be used.

The invention relates to a process of continuous culture of certain bacteria, preferably Pseudomonas C. on a suitable nutrient medium, utilizing inexpensive and readily available substrates, and employing culture media yielding high yields of the desired products. Pseudomonas sp., strain C has been deposited under NRRL B-8099.(U.S. Dep. of Agriculture culture collection).

Although the following description relates to the process of the invention exemplified with reference to Pseudomonas C, the process can be used, with certain modifications, if necessary, for the growth of other bacteria to yield single-cell proteins for the same purpose, suitable other bacteria being, for example, Pseudomonas methanica, Pseudomonas AM-1, Pseudomonas PRL-W4, Pseudomonas oxalaticus, Methylococcus capsulatus and the like.

According to a preferred embodiment of the present invention, the bacteria are grown on a culture medium comprising methanol or methanol and formaldehyde or methanol and formate as substantially the sole carbon source or sources; the growth being effected in continuous culture.

One of the above, or one of the above combinations, is used as sole carbon source, the culture medium being adapted so as to yield an optimum yield. Amongst critical additives according to the present invention are sources of copper ions. The concentraton of these is adjusted so as to give a predetermined concentration of copper ions in the culture medium. The range of copper ions, calculated as metallic copper, is advantageously about 2.5 micrograms ($\gamma$) to about 200 $\gamma$ per liter; the preferred range being about 10–100 $\gamma$/l.

The production of single-cell protein can be effected by growing a bacterium capable of utilizing methanol or methanol and formaldehyde or methanol and formate as carbon sources, on a culture medium comprising methanol as single carbon source, the culture being a continuous one, the medium containing a predetermined quantity of copper as set out above.

In all the above cases high yields of easily harvestable single-cell protein were obtained by the continuous growth of Pseudomonas C. With culture media comprising a suitable quantity of copper, as defined above, this bacterium gave good results with media comprising methanol and formaldehyde as carbon sources and with media comprising methanol and formate as carbon sources. In the last two cases the ratio of methanol to the other carbon source was in the range of from about 1:2 to about 100 to 1.

The temperature may be in the range of 30°–42° C. but highest yields are obtained in the range of 35°–38° C. The pH should be in the range of 5–8 for best results. For practical reasons, it may be advantageous to work at a temperature of 39°–42° C., although in this temperature range yields are not the highest obtainable.

It is clear that the culture medium used for the continuous culture according to the present invention must contain a suitable source of nitrogen, such as ammonia, nitrate or urea; and suitable salts. After growth, the cells are easily recovered by conventional means, such as centrifugation or the like, and can be used for the intended purposes.

Pseudomonas C has been described (Appl. Microbiol. 23, 135–140,1972). Additional characteristics are as follows: growth on fructose, melibiose and propanol; no growth on lactate, succinate or methylamine; can utilize urea as a nitrogen source.

According to the present invention, the continuous culture process gives increased yields (about 50–60% on methanol) and it is also possible to use formate or formaldehyde as substrates by using them together with methanol. As many industrial wastes contain formate and/or formaldehyde the process of the invention provides means for utilizing these as a course for the growth of valuable commercial products.

According to one embodiment of the present invention optimum conditions were determined for the culture of Pseudomonas C, in continuous culture, on a medium adapted to result in high yields. One of the critical parameters which was unexpectedly discovered was the quantity of copper necessary to maintain optimum growth conditions.

The present invention is illustrated in the following with reference to certain specific techniques and examples, and it is to be clearly understood that these are by way of example only and that these are to be construed in a non-limitative manner. The theory of continuous culture has been explained in the literature, for instance, Herbert, Elsworth and Telling, J. Gen. Microbiol. 14, 601–622, 1956.

DESCRIPTION OF THE PREFERRED EMBODIMENTS:

EXAMPLE 1

The various media used are as follows:

|  | MSM |  | MSM-M |  | M-3 | M-4 |
|---|---|---|---|---|---|---|
| $(NH_4)_2SO_4$ | 1.0 | gm | 1.0 | gm | 2.5 | 2.5 |
| $Na_2HPO_4$ | 0.21 |  | 2.1 |  | 0.3 | 2.1 |
| $NaH_2PO_4$ | 0.09 |  | 0.9 |  | 0.15 | 0.9 |
| $MgSO_4 . 7H_2O$ | 0.2 |  | 0.1 |  | 0.3 | 0.15 |
| KCl | 0.04 |  | 0.04 |  | 0.06 | 0.06 |
| $CaCl_2$ | 0.015 |  | 0.015 |  | 0.020 | 0.020 |
| $FeSO_4 . 7H_2O$ | 0.001 |  | 0.001 |  | 0.002 | 0.002 |
| $CuSO_4 . 5H_2O$ | 5 | micgm | 5 | m.gm. | 80 | 80 |
| $H_3BO_3$ | 10 |  | 10 |  | 20 | 20 |
| $MnSO_4 . 5H_2O$ | 10 |  | 10 |  | 20 | 20 |
| $ZnSO_4 . 7H_2O$ | 70 |  | 70 |  | 80 | 80 |

|   | MSM | MSM-M | M-3 | M-4 |
|---|---|---|---|---|
| $Na_2MoO_4$ | 15 | 15 | 20 | 20 |

Pseudomonas C was grown in shake flasks at 35° C. on MSM-M medium that had been sterilized by autoclaving, and to which was added 10 gm. methanol per liter. When this culture was growing well several milliliters was used to inoculate 50 ml of sterile MSM-M and M-4 media in 250 ml shake flasks which were innoculated with shaking at 32° C. The optical density at 650 mm was measured as a function of time, and 1OD unit equalled about 0.7 mg dry weight of cells per ml.

| Time(hrs) | MSM-M | M-4 |
|---|---|---|
| 0 | 0.13 | 0.14 |
| 1.5 | 0.25 | 0.23 |
| 2.6 | 0.45 | 0.39 |
| 5.0 | 1.0 | 0.88 |
| 6.0 | 1.1 | 1.3 |
| 8.0 | 1.1 | 2.3 |
| 10.0 | 1.1 | 3.9 |

Thus, medium M-4 yielded about 4 times more growth than medium MSM-M.

EXAMPLE 2

Pseudomonas C was grown in continuous culture on medium MSM, at 35° C with an agitation rate of 800 r.p.m. and an aeration rate of 1 vol. air/1 vol. medium-min. The dilution rate (ratio of medium flow rate to fermenter volume) was 0.32 $hr^{-1}$, and the pH was controlled at 7.0±0.1. The concentration of methanol in the inflowing medium was 2.0 gm/l., and at steady state the cell concentration was 0.46 gm/l. Supplementation of the medium with 75 microgram of $CuSO_4 \cdot 5H_2O$ per liter yielded a new steady state cell concentration of 1.05 gm/l, for a yield of 52.5% based on methanol.

EXAMPLE 3

Pseudomonas C was grown in continuous culture at a dilution rate of 0.35 $hr^{-1}$, at 35° C. with an agitation rate of 600 r.p.m. and an aeration rate of 0.5 vol./vol.-min., at a pH of 7.0±0.1. The medium was M-3 containing various concentrations of methanol and formaldehyde and steady state values were as follows:

| influent $M_2OH$ conc(g/l) | influent HCHO conc(g/l) | Cell. Conc. (g/l) | Yield* (%) |
|---|---|---|---|
| 1.00 | — | 0.54 | 56 |
| 1.02 | 0.1 | 0.59 | 55 |
| 1.12 | 0.5 | 0.72 | 46 |
| 1.25 | 1.0 | 0.88 | 40 |
| 1.50 | 2.0 | 0.98 | 29 |
| 2.00 | 4.0 | 1.21 | 22 |

*based on utilization of methanol plus formaldehyde.

EXAMPLE 4

Pseudomonas C was grown in continuous culture with the same experimental conditions as in Example 3, except that the medium contained 2.0 gm methanol per liter plus various concentrations of formic acid. The results were as follows:

| influent HCOOH conc(g/l) | Cell Conc. (g/l) | Yield* (%) |
|---|---|---|
| — | 1.09 | 55 |
| 0.3 | 1.10 | 51 |
| 1.0 | 1.18 | 45 |
| 2.0 | 1.25 | 39 |
| 3.0 | 1.26 | 31 |
| 4.0 | 1.27 | 28 |
| 5.0 | 1.27 | 23 |

*based on utilization of methanol plus formic acid.

EXAMPLE 5

Pseudomonas C was grown in continuous culture on threefold concentrated M-3 medium at 35° C., pH 7.0, agitation rate 1000 r.p.m., aeration rate 4-5 vol/vol-min., at a dilution rate of 0.35 $hr^{-1}$. The concentration of methanol in the inflowing medium was varied, and the steady state results were as follows:

| influent MeOH conc(g/l) | OD 650 mm | Yield* (%) |
|---|---|---|
| 2.5 | 1.6 | 56 |
| 5 | 3.9 | 55 |
| 10 | 6.5 | 53 |
| 15 | 11 | 53 |
| 20 | 13.3 | 51 |
| 25 | 16 | 49 |

*based on utilization of methanol.

EXAMPLE 6

Pseudomonas C was grown in continuous culture as in Example 5 with a methanol concentration of 10 gm/liter. The cell suspension leaving the growth vessel was cooled and harvested by centrifugation. The cell paste was dried in an oven at 105° C and the dried material was analyzed. The following results were obtained: Kjeldahl nitogen: 13.3%; Kjeldahl protein: (Nx6.25) 83%; biuret protein: 61%; Lowry protein: 67%; nucleic acids (by optical absorption of perchloric acid extracts): 16%. The amino acid composition of the protein was as follows (grams amino acid per 100 gm amino acids): alanine - 9.2; arginine - 6.3; aspartic acid - 10.4; half cysteine - 1.1; glutamic acid 13.1; glycine - 6.3; histidine - 2.5; isoleucine - 5.6; leucine - 8.1; lysine - 8.3; methionine - 2.6; phenylalanine - 4.0; proline - 3.7; serine - 3.5; threonine - 5.9; tyrosine - 2.9; valine - 6.7. Tryptophan was not determined.

Thus, Pseudomonas C is a good source of protein, and it is especially rich in lysine and in the sulfur-containing amino acids, methionine and cysteine. It can be usefully incorporated into feed mixtures for poultry, pigs, fish, calves and for adult ruminants. After appropriate treatment it can be used as component of human food, for example as meat extender, in sausages, as gruel and for other purposes where the addition of valuable proteins is indicated.

It is possible to culture under similar conditions *Pseudomonas methanica*, Pseudomonas AM-1, Pseudomonas PRL-W4, *Pseudomonas oxalaticus* and *Methylococcus capsulatus* and to obtain similar results.

We claim:

1. A process for the production of single cell protein comprising growing on a suitable culture medium which contains from 2.5 to 200 micrograms copper per liter, calculated as metal, by continuous culture, Pseudomonas C, there being used as sole carbon source methanol, methanol and formaldehyde, or methanol and formate, until a predetermined crop of single cell protein is obtained.

2. A process as claimed in claim 1, wherein the sole carbon source is methanol.

3. A process as claimed in claim 1, wherein the culture medium contains 10 to 100 micrograms copper per liter.

4. A process as claimed in claim 1, wherein the sole carbon source is methanol and formaldehyde.

5. A process as claimed in claim 1, wherein the sole carbon source is methanol and formate.

* * * * *